US00PP18286P3

(12) United States Plant Patent
Houbraken

(10) Patent No.: US PP18,286 P3
(45) Date of Patent: Dec. 4, 2007

(54) ***OSTEOSPERMUM* PLANT NAMED 'OSECMAPU'**

(50) Latin Name: *Osteospermum ecklonis*
Varietal Denomination: Osecmapu

(75) Inventor: Anna M. W. P. Houbraken, Enkhuizen (NL)

(73) Assignee: Syngenta Seeds B.V., Enkhuizen (NL)

( * ) Notice: Subject to any disclaimer, the term of this patent is extended or adjusted under 35 U.S.C. 154(b) by 0 days.

(21) Appl. No.: 11/430,146

(22) Filed: May 8, 2006

(65) Prior Publication Data

US 2007/0261146 P1 Nov. 8, 2007

(51) Int. Cl.
*A01H 5/00* (2006.01)

(52) U.S. Cl. ..... Plt./360

(58) Field of Classification Search ..... Plt./360
See application file for complete search history.

(56) References Cited

U.S. PATENT DOCUMENTS

| | | | | | |
|---|---|---|---|---|---|
| PP15,491 | P3 | * | 1/2005 | Oud | Plt./360 |
| PP16,389 | P3 | * | 3/2006 | Larsen | Plt./360 |
| PP17,275 | P2 | * | 12/2006 | Larsen | Plt./360 |
| 2005/0022279 | P1 | * | 1/2005 | Larsen | Plt./360 |

OTHER PUBLICATIONS

UPOV ROM GTITM Computer Database, GTI Jouve Retrieval 2006/04 Citations for 'Osecmapu'.*

* cited by examiner

*Primary Examiner*—Wendy C. Haas
(74) *Attorney, Agent, or Firm*—Bruce Vrana

(57) ABSTRACT

A new *Osteospermum* plant particularly distinguished by its mounding plant habit, early flowering with deep purple colored ray florets and large inflorescences.

1 Drawing Sheet

Latin name of the genus and species of the plant claimed: *Osteospermum ecklonis*.
Varietal denomination: 'Osecmapu'.

BACKGROUND OF THE NEW PLANT

The present invention relates to a new and distinct cultivar of *Osteospermum* plant, botanically known as *Osteospermum ecklonis*.

The new *Osteospermum* is propagated by cuttings resulting from an open pollinated population from a proprietary *Osteospermum ecklonis* seedling selection as the female, or seed, parent identified as breeder's code 'E0202-3' (unpatented). Breeder's code of new plant is 'G0122-3.'

The new *Osteospermum* was discovered and selected as a single flowering plant within the progeny of the stated population grown in Enkhuizen, Netherlands, in 2002. The new *Osteospermum* plant has been repeatably asexually reproduced by cuttings in Enkhuizen, Netherlands over a period of 3 years. It has been found to retain its distinctive characteristics through successive propagations, and this novelty appears to be firmly fixed.

DESCRIPTION OF THE DRAWING

This new *Osteospermum* plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new *Osteospermum* plant. The data which defines these characteristics were collected from asexual reproductions carried out in Enkhuizen, Netherlands. The plant history was taken on 25 weeks old plants. The instant plant was grown indoors in a 10.5 cm container and transplanted into the open field in week 20.

Color references are primarily to The R.H.S. Colour Chart of The Royal Horticultural Society of London, edition 2001.

TABLE 1

DIFFERENCES BETWEEN THE NEW CULTIVAR 'OSECMAPU' AND TWO SIMILAR CULTIVARS

| | 'Osecmapu' | 'Osoutis' (U.S. Pat. No. 15,491) | 'Wild Side' (Not patented) |
|---|---|---|---|
| Plant height | 26 cm | 22 cm | 38 cm |
| Plant width | 60 cm | 24 cm | 52 cm |
| Flower colour | Deep Purple | Purple fading | Deep Purple |
| Flower size | 5.5-6.2 cm | 5 cm | 5 cm |

The plant: Classification — Botanical: *Osteospermum ecklonis*.

Parentage:

*Female parent.*—Proprietary seedling selection 'E0202-3'.

*Male parent.*—Female is open pollinated so male is unknown.

Plant description:

*Growth habit.*—Round, mounding.

*Plant height.*—26 cm.

*Spreading area of plant.*—60 cm.

*Strength.*—Strong growth.

*Branching character.*—Freely branching, 30 lateral branches without pinching.

*Blooming period.*—From May until October.

The stem:

*Length.*—25 cm.

*Diameter.*—4 mm.

*Internode length.*—1.5 mm

*Texture.*—Glabrous.

*Color.*—RHS 144A.

*Anthocyan.*—Bit present.

The foliage:

*Shape.*—Single leaves, alternate and elliptic, apex: broadly acute base: attenuate, margin: irregular serration.

*Number of leaves per lateral branches.*—50.

*Texture.*—Glabrous, leathery.

*Leaf.*—Color — Upper side: RHS 137A. Color — Under side: RHS 137C. Length: Young 18–20 mm, mature 45–55 mm. Width: Young 6–7 mm, mature 16–18 mm.

*Petiole.*—Absent.

The inflorescence:

*Number of inflorescences per mature plant.*—110.

*Inflorescence bud.*—Form: Ovoid. Length: 10–15 mm. Width: 9–10 mm. Color: RHS 79A+2C.

*Inflorescence lastingness on the plant.*—Around 5 days depending on the temperature.

*Inflorescence.*—Diameter: 55–62 mm. Disc diameter: 12 mm.

*Inflorescence depth.*—15 mm.

*Fragrance.*—No fragrance.

*Disc florets.*—Shape: Tubular, elongated. Apex: Five pointed. Length: 8 mm. Width: 1 mm. Number of the disc florets per inflorescence: 55. Color: RHS 79A.

*Ray florets.*—Length: 28 mm. Width: 9 mm. Shape: Capitulum with one series of ray florets. Color Upper surface: RHS 72A. Middle surface: RHS 72A. Lower surface: RHS N79A. Number of ray florets: 19–20. Shape — Apex: Rounded. Base: Acute. Margin: Entire. Texture: Satiny.

*Peduncles.*—Length: 30–45 mm. Texture: Sturdy, tiny hairs. Color: RHS N77A+144A. Diameter: 1.5 mm. Shape: Round.

*Phyllaries.*—Texture: Rough, tiny hairs. Number of phyllaries: 18. Color: RHS 143A. Length: 8–10 mm. Margin: Entire. Width: 1 mm. Apex: Acute. Shape: Ligulate. Color: RHS 137C both sides.

Reproductive organs:

*Androecium.*—Appearance: Present on disc florets only. Shape: Oblong, five stamen fused to one. Length: 3 mm. Width: 1 mm. Pollen color: RHS 25A. Total no. of anthers: 64.

*Gynoecium.*—Appearance: Present on both ray and disc florets. Pistil number: One pistil per ray or disc floret. Pistil length: 4 mm. Stigma color: RHS 77A. Stigma shape: Bipartite.

Seed development: Seed development has been observed on plants of the new *Osteospermum.*

*Amount of seeds produced.*—Moderate.

*Seed length.*—6 mm.

*Diameter.*—3 mm.

*Color.*—RHS 200A.

*Shape.*—Elliptic.

Disease resistance: Under commercial conditions, plants of the new *Osteospermum* are resistant to fungal pathogens common to *Osteospermum.*

What is claimed is:

1. A new and distinct variety of *Osteospermum* plant, substantially as illustrated and described herein.

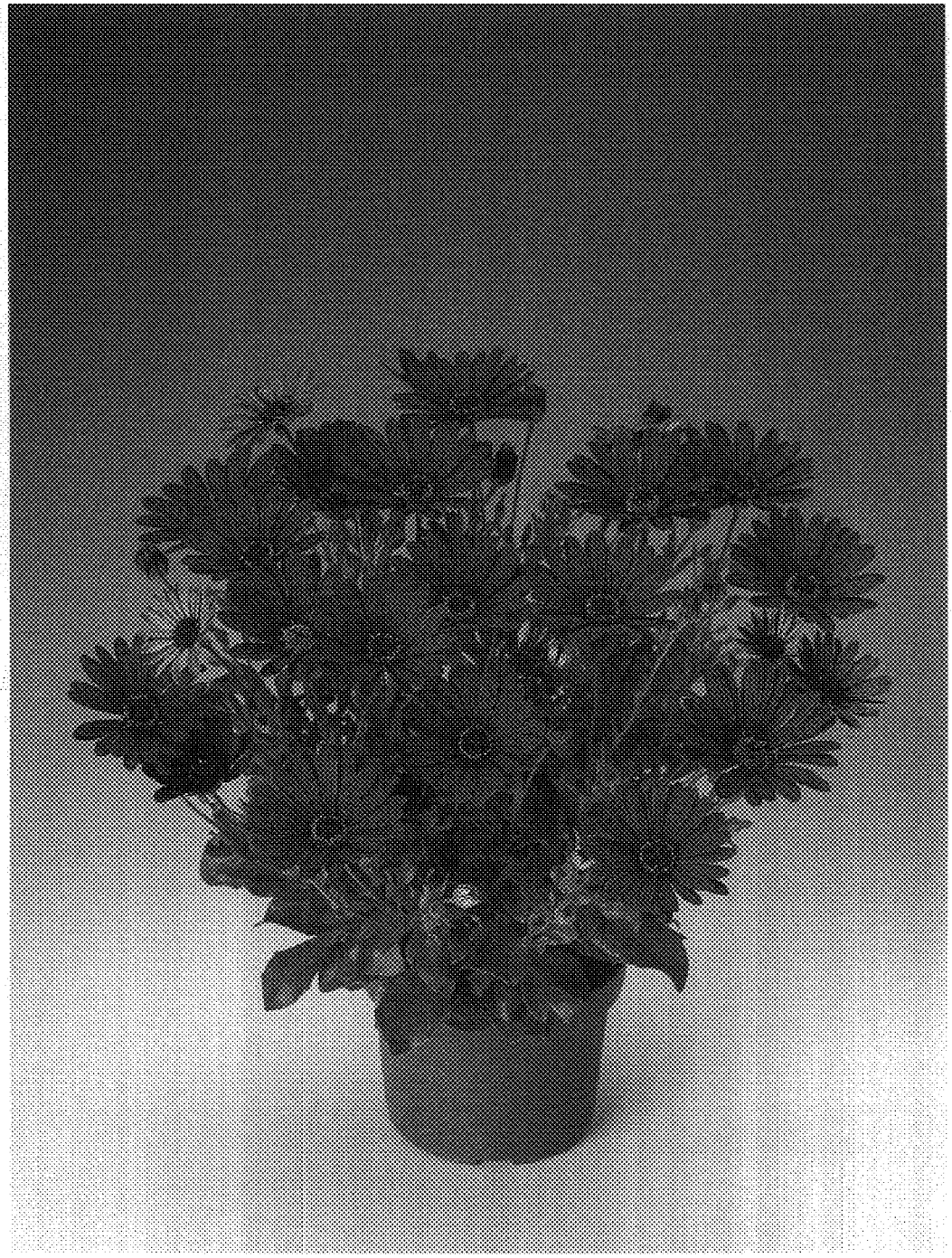

* * * * *